(12) United States Patent
Okano et al.

(10) Patent No.: US 10,434,219 B2
(45) Date of Patent: Oct. 8, 2019

(54) METHOD OF TREATMENT USING CORNEAL EPITHELIUM FORMING CELL SHEETS

(71) Applicants: CellSeed Inc., Tokyo (JP); Kohji Nishida, Osaka (JP)

(72) Inventors: Teruo Okano, Chiba (JP); Kohji Nishida, Osaka (JP); Masayuki Yamato, Tokyo (JP)

(73) Assignees: CELLSEED INC., Tokyo (JP); Kohji Nishida, Osaka (JP)

( * ) Notice: Subject to any disclaimer, the term of this patent is extended or adjusted under 35 U.S.C. 154(b) by 0 days.

(21) Appl. No.: 15/859,304

(22) Filed: Dec. 29, 2017

(65) Prior Publication Data

US 2018/0126040 A1    May 10, 2018

Related U.S. Application Data

(62) Division of application No. 10/544,541, filed as application No. PCT/JP2004/001274 on Feb. 6, 2004.

(30) Foreign Application Priority Data

Feb. 6, 2003 (JP) .................. 2003-068899
Feb. 14, 2003 (JP) .................. 2003-079100

(51) Int. Cl.
*A61L 27/38* (2006.01)
*C12N 5/079* (2010.01)

(52) U.S. Cl.
CPC ....... *A61L 27/3891* (2013.01); *A61L 27/3804* (2013.01); *A61L 27/3839* (2013.01); *A61L 27/3895* (2013.01); *C12N 5/0621* (2013.01); *A61L 2430/16* (2013.01); *C12N 2539/10* (2013.01)

(58) Field of Classification Search
CPC ............. A61L 27/3804; A61L 27/3839; A61L 27/3891; A61L 2430/16; A61L 27/3895; C12N 2539/10; C12N 5/0621
See application file for complete search history.

(56) References Cited

U.S. PATENT DOCUMENTS

| | | | |
|---|---|---|---|
| 4,718,420 A | 1/1988 | Lemp | |
| 4,772,283 A | 9/1988 | White | |
| 5,284,766 A | 2/1994 | Okano et al. | |
| 5,837,278 A | 11/1998 | Geistlich | |
| 6,956,077 B1 | 10/2005 | Akiyama et al. | |
| 7,470,424 B2 | 12/2008 | Kataoka et al. | |
| 7,691,369 B2 | 4/2010 | Kataoka et al. | |
| 2003/0036196 A1 | 2/2003 | Okano et al. | |
| 2004/0009566 A1 | 1/2004 | Okano et al. | |
| 2004/0028657 A1 | 2/2004 | Okano et al. | |
| 2004/0092492 A1 | 5/2004 | Ring et al. | |
| 2004/0197907 A1 | 10/2004 | Kataoka et al. | |
| 2006/0234377 A1 | 10/2006 | Okano et al. | |
| 2006/0240552 A1 | 10/2006 | Okano et al. | |
| 2007/0148137 A1 | 6/2007 | Okano et al. | |
| 2008/0118474 A1 | 5/2008 | Okano et al. | |
| 2008/0131476 A1 | 6/2008 | Kanzaki et al. | |
| 2008/0226692 A1 | 9/2008 | Sato et al. | |
| 2008/0289052 A1 | 11/2008 | Okano et al. | |
| 2009/0011504 A1 | 1/2009 | Kataoka et al. | |
| 2011/0229962 A1 | 9/2011 | Mizutani et al. | |

FOREIGN PATENT DOCUMENTS

| | | |
|---|---|---|
| JP | 2002-331025 | 11/2002 |
| JP | 2003-038170 | 2/2003 |
| MX | 9831316 | 7/1998 |
| WO | 1999/37752 | 7/1999 |
| WO | 2001/68799 | 9/2001 |
| WO | 2001/80760 | 11/2001 |
| WO | 2002/10349 | 2/2002 |
| WO | 2004/069295 | 8/2004 |
| WO | 2004/070023 | 8/2004 |
| WO | 2004/073761 | 9/2004 |

OTHER PUBLICATIONS

Chen et al. "Amniotic membrane transplantation for severe neurotrophic corneal ulcers" Br. J. Ophthalmol. 84:826-833 (2000).
Elsevier Health: Anterior Segment Surgery and Complications: "Cataract extraction and intraocular lens implantation" Chapter 10, Published on the web at—http://www3.us.elsevierhealth.com/HHS/reqoph/RapuanoCh1 O.pdf, pp. 1-68 (2002).
Endo et al. "Human amniotic membrane, like corneal epithelial basement membrane, manifests the α5 chain of type IV collagen" Invest. Ophthalmol. Vis. Sci. 45:1771-1774 (2004).
Forbes et al. "Split-thickness buccal mucous membrane grafts and β irradiation in the treatment of recurrent pterygium" Br. J. Ophthalmol. 82:1420-1423 (1998).
Gipson & Grill "A technique for obtaining sheets of intact rabbit corneal epithelium" Invest. Ophthalmol. Vis. Sci. 23:269-273 (1982).
Hirose et al. "Temperature-responsive surface for novel co-culture systems of hepatocytes with endothelial cells: 2-D patterned and double layered co-cultures" Yonsei Med. J. 41:803-813 (2000).
Hirose et al. "Creation of designed shape cell sheets that are noninvasively harvested and moved onto another surface" Biomacromol. 1:377-381 (2000).

(Continued)

*Primary Examiner* — Satyendra K Singh
(74) *Attorney, Agent, or Firm* — Nixon & Vanderhye P.C.

(57) ABSTRACT

A diseased site where an anterior segment tissue is partly or entirely damaged or deficient can be treated using a corneal epithelium forming cell sheet that will adhere well to the anterior segment tissue. To attain this objective, a corneal epithelium forming cell sheet is produced by a process comprising the steps of cultivating under specified conditions corneal epithelium forming cells on a cell culture support comprising a substrate having its surface covered with a temperature responsive polymer of which the hydrating force varies in a temperature range of 0° C.-80° C., optionally stratifying the layer of cultured cells, and thereafter, (1) adjusting the temperature of the culture solution to either above an upper critical dissolution temperature or below a lower critical dissolution temperature, (2) bringing the cultured corneal epithelium forming cells into close contact with a carrier, and (3) detaching the sheet together with the carrier under specified conditions.

7 Claims, No Drawings

(56) References Cited

OTHER PUBLICATIONS

Kinoshita "[Ocular surface reconstruction by tissue engineering]" Nippon Ganka Gakkai Zasshi 106:837-868, abstract only (2002).

Koizumi "Cultivated corneal epithelial transplantation for ocular surface reconstruction in acute phase of Steven-Johnson syndrome case reports and small case series" Arch. Ophthalmol. 119:298-300 (2001).

Koizumi et al. "Cultivated corneal epithelium stem cell transplantation in ocular surface disorders" Ophthalmol. 108:1569-1574 (2001).

Kushida "Biomaterial no Kirikudaku Saisei Ikogaku no Sekai Toseki kara Bio Jinkojin e" Igaku no Ayumi 195:205-206 (2000).

Kushida et al. "Two-dimensional manipulation of differentiated Madin-Darby Canine Kidney (MDCK) cell sheets: the noninvasive harvest from temperature-responsive culture dishes and transfer to other surfaces" J. Biomed. Mater. Res. 54:37-46 (2001).

Lindberg et al. "In vitro propagation of human ocular surface epithelial cells for transplantation" Invest. Ophthal. Vis. Sci. 34:2672-2679 (1993).

Nakamura et al. "The successful culture and autologous transplantation of rabbit oral mucosal epithelial cells on amniotic membrane" Invest. Ophthalmol. Vis. Sci. 44:106-116 (2003).

Nishida "Johi-Hifu Saisei no Kiso to Rinsho, Kakumaku no Saisei Iryo" Gekkan Med. Sci. Digest 28:577-581 (2002).

Nishida "Biomaterial to Atarashii Ganka Iryo Kakumakujohi, Kakumakunaihi no Saisei Iryo" Biomaterial 20:259-268 (2002).

Orwin & Hubel "In vitro culture characteristics of corneal epithelial, endothelial, and keratinocyte cells in a native collagen matrix" Tissue Eng. 6:307-319 (2000).

Schwab "Cultured corneal epithelia for ocular surface disease" Trans. Am. Ophthal. Soc. 97:891-986, abstract only (1999).

Shimizu et al. "Fabrication of pulsatile cardiac tissue grafts using a novel 3-dimensional cell sheet manipulation technique and temperature-responsive cell culture surfaces" Circ. Res. 90:e40-e48 (2002).

Tsai et al. "Reconstruction of damaged corneas by transplantation of autologous limbal epithelial cells" New Engl. J. Med. 343:86-93 (2000).

Yamato et al. "Thermo-responsive culture dishes allow the intact harvest of multilayered keratinocyte sheets without dispase by reducing temperature" Tissue Eng. 7:473-480 (2001).

Yamato "Saibo Sheet Kogaku no Sosei" Biomaterial 21:46-52 (2003).

EPO search report for related EP 04708896.8, four pages (dated Jun. 2009).

EPO search report and search opinion for related EP 11192961.8, eight pages (dated Apr. 2012).

International Search Report for PCT/JP2004/001274, two pages (dated May 2004).

Int'l Prel. Report on Patentability for PCT/JP2004/001274, eight pages (dated Feb. 2006).

METHOD OF TREATMENT USING CORNEAL EPITHELIUM FORMING CELL SHEETS

This is a division of application Ser. No. 10/544,541, filed Jun. 15, 2006, pending; which is the U.S. national stage of Application No. PCT/JP2004/001274, filed Feb. 6, 2004; which designated the U.S. and claims priority benefit of JP 2003-079100, filed Feb. 14, 2003, and JP 2003-068899, filed Feb. 6, 2003; the entire contents of each of which are hereby incorporated by reference.

TECHNICAL FIELD OF THE INVENTION

This invention relates to corneal epithelium forming cell sheets in biology, medicine and other fields, as well as processes for producing such sheets, and therapeutic methods using them.

BACKGROUND ART

With marked advances in medical technology, it has recently become popular to perform organ transplants, i.e., replacing a difficult-to-treat organ with another person's organ. The organs that can be transplanted are quite diverse and include the skin, cornea, kidney, liver and heart, and in addition, the postoperative progress of organ transplants has improved so remarkably that they are already becoming established as a medical procedure. Keratoplasty is one example and as early as 40 years ago, an eye bank was organized in Japan to start transplanting activities. However, as of today, the number of donors in Japan is very small and notwithstanding the fact that there are annually about 20,000 patients who need keratoplasty, only a tenth of them (ca. 2,000 in number) can actually be treated by that procedure. Although keratoplasty is a virtually established procedure, it suffers the problem of shortage in donors, giving rise to the need for the development of a next-generation medical procedure.

With this background, attention has been drawn to the procedure of directly transplanting artificial substitutes or cells that were cultured into assembly. Typical examples of this approach are the artificial skin and the cultured skin. However, the artificial skin using synthetic polymers has the potential to cause rejection and other side effects that make it undesirable as skin grafts. On the other hand, the cultured skin is prepared by cultivating a portion of the normal skin of the patient until it grows to a desired size, so it can be used without the risk of causing rejection and any other side effects and may well be described as the most natural masking agent.

Conventionally, such cell culture has been performed either on the surface of glass or on the surface of synthetic polymers that were subjected to a variety of treatments. For example, a variety of polystyrene vessels that were subjected to surface treatments such as γ-ray irradiation and silicone coating have become popular for use in cell culture. Cells that have been cultivated to grow on those vessels for cell culture are detached and recovered from the surfaces of the vessels by treatment with proteinases such as trypsin or chemical reagents.

However, it has been pointed out that the recovery of grown cells by treatment with chemical reagents involves some disadvantages such as the processing steps becoming cumbersome to increase the chance of contamination by impurities and the grown cells becoming denatured or damaged by the chemical treatment to have their inherent functions injured. In order to overcome these disadvantages, several techniques have been proposed to date.

JP 2-23191 B describes a method for producing a transplantable membrane of keratin tissue which comprises the steps of cultivating human neonatal keratinized epidermic cells in a culture vessel under conditions that enable a membrane of keratin tissue to form on the surface of the vessel and detaching the membrane of keratin tissue using an enzyme. Specifically, with 3T3 cells used as a feeder layer, the epidermic cells are grown and stratified as a cell sheet which is recovered using the proteinase dispase. However, the method described in JP 2-23191 B has had the following defects.

(1) Dispase is of microbial origin and the recovered cell sheet needs to be washed thoroughly.
(2) The conditions for dispase treatment differ from one batch of cell culture to another and great skill is required in the treatment.
(3) The cultured epidermic cells are pathologically activated by dispase treatment.
(4) The extracellular matrix is decomposed by dispase treatment.
(5) As the result, the diseased site to which the cell sheet has been grafted is prone to infection.

In addition to these defects of the prior art method, anterior segment related cells that are contemplated in the present invention, such as corneal epithelial cells, corneal endothelial cells and conjunctival epithelial cells, do not have as strong intercellular binding as dermal cells and have had the problem that cultivated cells cannot be detached and recovered as a single sheet even if the dispase is employed.

In order to solve this problem, a technique has recently been devised, according to which corneal epithelial cells or conjunctival epithelial cells are cultured into assembly on an amnion deprived of the spongy layer and the epithelial layer and the assembly is used as a cell graft together with the amnion (JP 2001-161353 A). Since the amnion has adequate strength as a membrane but has no antigenicity, it is favorable as a support of cell grafts; however, the amnion is not inherently in the eye and in order to construct a more precise intraocular tissue, it has been desired that a satisfactorily strong sheet be prepared solely from the intraocular cells and that the sheet have direct contact with the corneal stromal tissue.

In Japanese Patent Application No. 2001-226141, anterior segment related cells are cultivated on a cell culture support comprising a substrate having its surface coated with a temperature responsive polymer having an upper or lower critical temperature of 0-80° C. at which it dissolves in water and, if necessary, the cultured cell layer is stratified by the usual method and the cultured cell sheet is detached by merely changing the temperature of the support. The detached cell sheet has adequate strength. It also retains a basement membrane-like protein and, compared to the cell sheet recovered by the above-described dispase treatment, it obviously has a better take on the tissue. However, considering the need to reduce the actual burden on patients, a further improvement on the take has been desired.

Various methods have recently been proposed in clinical settings, too. For example, WO 98/31316 has proposed a technique that utilizes a cultured corneal epithelial cell sheet in the treatment of myopia by the PRK method or the LASIK method. However, the cultured corneal epithelial sheet described in WO 98/31316 has been detached by the dispase treatment and has had the problem that it adheres so poorly to the laser ablated corneal tissue that no significant therapeutic efficacy is achievable.

In a news article in the May 10, 2001 issue of *the Mainichi*, there was proposed a technique by which a cultured oral mucosa rather than the cornea was pasted to a patient suffering a corneal disease with a view to promoting corneal regeneration in the patient. However, the cultured oral mucosa reported in the article was detached by dispase treatment and had the problem that it adhered so poorly to the corneal tissue of the patient that no significant therapeutic efficacy would be achievable.

The present invention has been accomplished with a view to solving the aforementioned problems of the prior art. Therefore, the present invention has as an object providing a corneal epithelium forming cell sheet that adheres well to an anterior segment tissue. Other objects of the present invention are to provide a process for producing the cell sheet and a method of using it.

SUMMARY OF THE INVENTION

In order to attain the stated objects, the present inventors engaged in R&D activities taking various angles of study. As a result, the inventors found that a corneal epithelium forming cell sheet that would adhere very well to a living tissue could be obtained by a process comprising the steps of cultivating corneal epithelium forming cells under specified conditions on a cell culture support comprising a substrate having its surface covered with a specified temperature responsive polymer, thereafter adjusting the temperature of the culture solution to either above an upper critical dissolution temperature or below a lower critical dissolution temperature, bringing the cultured corneal epithelium forming cell sheet into close contact with a specified carrier, and detaching the sheet together with the carrier while care is taken to inhibit the shrinkage of the sheet. The present invention has been accomplished on the basis of this finding.

Thus, the present invention first provides a corneal epithelium forming cell sheet that will adhere well to an anterior segment tissue and which has been brought into close contact with a carrier.

The present invention also provides a process for producing a corneal epithelium forming cell sheet that will adhere very well to a living tissue, comprising the steps of cultivating corneal epithelium forming cells on a cell culture support comprising a substrate having its surface covered with a temperature responsive polymer of which the hydrating force varies in a temperature range of 0-80° C., optionally stratifying the layer of cultured cells by the usual method, and thereafter, (1) adjusting the temperature of the culture solution to either above an upper critical dissolution temperature or below a lower critical dissolution temperature,
(2) bringing the cultured corneal epithelium forming cells into close contact with a carrier, and
(3) detaching the sheet together with the carrier.

In addition, the present invention provides the above-described corneal epithelium forming cell sheet that will adhere very well to a living tissue for the treatment of a tissue that has become deficient and/or wounded to a deeper area.

Further in addition, the present invention provides a method of treatment characterized in that the above-described corneal epithelium forming cell sheet which will adhere very well to a living tissue is grafted to a tissue that has become deficient and/or wounded to a deeper area.

Still further, the present invention provides a corneal epithelium forming cell sheet that is useful not only in the medical field but also as cells for safety assessment of chemical substances, poisons or medicines.

MODES FOR CARRYING OUT THE INVENTION

As described above, the present invention provides a corneal epithelium forming cell sheet placed in close contact with a carrier. The term "corneal epithelium forming cell sheet" as used herein covers not only a regenerated corneal epithelial cell sheet formed from corneal epithelial cells but also a corneal epithelium substitute cell sheet formed from cells other than corneal epithelial cells.

If a regenerated corneal epithelial cell sheet is used as the corneal epithelium forming cell sheet of the present invention, corneal epithelial cells and stem cells thereof may be mentioned as cells suitable for use but the applicable cells are by no means limited in type.

If a corneal epithelium substitute cell sheet is used as the corneal epithelium forming cell sheet of the present invention, oral mucosa cells present on the buccal membrane or the gingival, hair root cells or conjunctival epithelial cells may be mentioned as cells suitable for use; those cells may be taken individually or in admixture of two or more kinds or in admixture thereof with corneal epithelial cells, but the applicable cells are by no means limited in type. When preparing those cell sheets, there is no need to add any special additives during cultivation of corneal epithelium substitute cells and if oral mucosa cells are used as corneal epithelium substitute cells, they may be cultivated by standard methods of cultivating oral mucosa cells to prepare a cultured cell sheet and the like.

In the context of the present invention, the corneal epithelium forming cell sheet may be single-layered or stratified. Therefore, in the case where it is a regenerated corneal epithelial cell sheet, both a single-layered and a stratified sheet of regenerated corneal epithelial cells are included; and in the case of a corneal epithelium substitute cell sheet, both a single-layered and a stratified sheet of corneal epithelium substitute cells are included. In other words, the corneal epithelium forming cell sheet may be whichever of a single-layered and a stratified sheet of regenerated corneal epithelial cells or corneal epithelium substitute cells.

In the present invention, the regenerated corneal epithelial cell sheet means a sheet that is obtained by cultivating a single layer of the above-described various cells on a culture support and thereafter detaching the layer from the support; the stratified sheet means a sheet that is obtained by stratifying the regenerated corneal epithelial cell sheet either on its own or in combination with a sheet or sheets of other cells.

Further in the present invention, the corneal epithelium substitute cell sheet means a sheet that is obtained by cultivating a single layer of the above-described various cells on a culture support and thereafter detaching the layer from the support; the stratified sheet means a sheet that is obtained by stratifying the corneal epithelium substitute cell sheet either on its own or in combination with a sheet or sheets of other cells.

The corneal epithelium forming cell sheet in the present invention is such that it has not been damaged during cultivation by proteinases typified by dispase and trypsin. Therefore, the corneal epithelium forming cell sheet as detached from the substrate retains the intercellular desmosome structure, has only a few structural defects, and features high strength. In addition, the sheet of the present invention is characterized in that the basement membrane-like protein formed between cell and substrate during cultivation has not been destroyed by enzyme. Hence, the sheet can attach satisfactorily to the living tissue of the diseased site to which it has been grafted and this enables an efficient treatment to be performed. This property of adhering very effectively to living tissues is called "high adherence" in the present invention.

This is described below more specifically. If an ordinary proteinase such as trypsin is employed, the intercellular desmosome structure and the basement membrane-like protein between cell and substrate are hardly retained and, hence, the cell sheet is detached with the cells separated into discrete masses. As for the proteinase dispase, the cell sheet can be detached with 10-60% of the intercellular desmosome structure being retained; however, almost all of the basement membrane-like protein between cell and substrate is destroyed and the cell sheet obtained has only low strength. In contrast, the cell sheet of the present invention keeps at least 80% of each of the desmosome structure and the basement membrane-like protein intact, thus providing the various advantages described above. Therefore, the above-mentioned property of "high adherence" structurally refers to a state where at least 80% of the desmosome structure and/or the basement membrane-like protein is kept intact.

The corneal epithelium forming cell sheet in the present invention shows a very good take on or "high adherence" to the anterior segment tissue which is a living tissue. The present inventors have found that in order for that property to be exhibited, it is also necessary to inhibit the shrinkage of the regenerated corneal epithelial cell sheet, either single-layered or stratified, as detached from the support's surface. Desirably, the shrinkage of the corneal epithelium forming cell sheet is no more than 20% in length in any of the directions in the sheet, preferably 10% or less, and more preferably 5% or less. If the shrinkage is more than 20% in length in any of the directions of the sheet, the detached cell sheet will become slack; in such a slack state, the sheet cannot be brought into close contact with the living tissue and the "high take" intended by the present invention is not attainable.

The method of inhibiting the shrinkage of the corneal epithelium forming cell sheet is not limited in any particular way as long as it will not cause the cell sheet to shrink; in one example, an annular carrier with a cutout in the center is placed in close contact with the corneal epithelium forming cell sheet, which is then detached from the support together with the carrier.

The carrier which is to be placed in close contact with the corneal epithelium forming cell sheet is a structure that keeps the cell sheet of the present invention from shrinking and may be realized by a polymer membrane or a structure molded from a polymer membrane, or a metallic fixture. If a polymer is to be used as the carrier material, specific examples include polyvinylidene difluoride (PVDF), polypropylene, polyethylene, celluloses, cellulose derivatives, papers, chitin, chitosan, collagen, urethane, etc.

The term "close contact" as used herein refers to such a state that the cell sheet does not shrink by slipping or moving on the carrier along the interface between the cell sheet and the carrier; the two members may be placed in close contact by being bound physically or with an intervening liquid (e.g. the culture solution or other isotonic fluid) in between.

The shape of the carrier is not limited in any particular way but if the corneal epithelium forming cell sheet obtained is grafted together with a carrier that has a cutout in a selected area which is about the same size as or larger than the site of grafting, great convenience is offered since the cell sheet is fixed only to the periphery of the cutout and just needs to be pressed through it to contact the site of grafting.

The cell sheet of the present invention is obtained by inoculating corneal epithelium forming cells on a substrate's surface and thereafter cultivating them for a period no longer than 21 days, preferably no longer than 15 days, more preferably no longer than 10 days, after the cells have reached confluence on the substrate's surface. If the period of cultivation is longer than 21 days after the cells have reached confluence, the activity of the cells in the bottommost layer in the detached corneal epithelium forming cell sheet drops and the sheet's adherence accordingly decreases with the result that the "high take" which characterizes the present invention is not attainable.

The corneal epithelium forming cell sheet of the present invention may be used to treat not only diseased sites where the anterior segment tissue is partly or entirely damaged or deficient as in corneal erosion and corneal ulceration but also binocular refractory conjunctival diseases without corneal epithelial cells. The anterior segment tissue as referred to in the present invention is not limited in any particular way as long as it is associated with the anterior segment but it generally includes the corneal epithelial tissue, Bowman's assembly, and the corneal stromal tissue. The refractory conjunctival diseases as referred to above include, for example, Stevens-Johnson syndrome, ocular pemphigus, burn, alkali corrosion, and acid corrosion.

As described above, the corneal epithelium forming cell sheet in the present invention is a cell sheet that can adhere very effectively to the anterior segment tissue which is a living tissue and it has not been possible at all to obtain it by the prior art.

The present invention also provides a process for producing the above-described corneal epithelium forming cell sheet of the invention. Briefly, it provides a process for producing a corneal epithelium forming cell sheet, comprising the steps of cultivating corneal epithelium forming cells on a cell culture support comprising a substrate having its surface covered with a temperature responsive polymer of which the hydrating force varies in a temperature range of 0-80° C., optionally stratifying the layer of cultured cells by the usual method, and thereafter, (1) adjusting the temperature of the culture solution to either above an upper critical dissolution temperature or below a lower critical dissolution temperature,
(2) bringing the cultured corneal epithelium forming cells into close contact with a carrier, and
(3) detaching the sheet together with the carrier.

The corneal epithelium forming cell sheet obtained by this method is characterized in that it has "high adherence" to living tissues.

The temperature responsive polymer which is used to cover the substrate of the cell culture support is characterized in that its hydrating power varies in a temperature range of 0-80° C., more preferably 20-50° C. One version of this temperature responsive polymer is such that it has an upper or lower critical dissolution temperature of 0° C.-80° C., more preferably 20° C.-50° C., in aqueous solution. Beyond 80° C., cells may die, which is not preferred. Below 0° C., the cell growth rate will generally drop by an extreme degree or cells will die, which also is not preferred.

In the present invention, the corneal epithelium forming cell sheet is preferably subjected to low-temperature treatment as it is detached from the cell culture support. For the low-temperature treatment that is to be performed in the present invention, the preferred temperature condition is in the range of 0° C.-30° C. and the preferred treatment time is in the range from two minutes to an hour; it should, however, be noted that these are not the sole examples of the temperature and time that can be employed in the invention. An example of preferred conditions for the low-temperature treatment is a 30-min incubation at 20° C.

The temperature responsive polymer to be used in the present invention may be a homopolymer or a copolymer. Examples of such polymers include the polymers described in JP 2-211865 A. Specifically, they are obtained by homo- or copolymerization of the following monomers. Monomers that can be used include, for example, (meth)acrylamide compounds, N- (or N,N-di)alkylsubstituted (meth)acrylamide derivatives, and vinyl ether derivatives; in the case of copolymers, any two or more of those monomers may be used. In addition, those monomers may be copolymerized with other monomers, or polymers may be grafted together or copolymerized, or alternatively, mixtures of polymers and copolymers may be employed. If desired, the polymers may be crosslinked to the extent that will not impair their properties.

The substrate that is to be covered with the temperature responsive polymer may be chosen from among the glass, modified glass, compounds such as polystyrene and poly (methyl methacrylate), and all other substances that can generally be given shape, as exemplified by polymer compounds other than those compounds, and ceramics.

The method of covering the support with the temperature responsive polymer is not limited in any particular way but one may follow the methods described in JP 2-211865 A. Specifically, the covering operation can be achieved by either subjecting the substrate and the above-mentioned monomers or polymers to electron beam (EB) exposure, γ-ray irradiation, ultraviolet irradiation, plasma treatment, corona treatment or organic polymerization reaction or by means of physical adsorption as effected by application of coating solutions or the kneading step.

The coverage of the temperature responsive polymer is suitably in the range of 0.4-4.5 μg/cm$^2$, preferably 0.7-3.5 μg/cm$^2$, more preferably 0.9-3.0 μg/cm$^2$. If the coverage of the temperature responsive polymer is less than 0.2 μg/cm$^2$, the cells on the polymer will not easily detach even if they are given a stimulus and the operating efficiency is considerably lowered, which is not preferred. If, on the other hand, the coverage of the temperature responsive polymer is greater than 4.5 μg/cm$^2$, cells will not easily adhere to the covered area and adequate adhesion of the cells becomes difficult to achieve.

The morphology of the support in the present invention is not limited in any particular way and may be exemplified by a dish, a multi-plate, a flask or a cell insert. Among these, a cell insert is particularly advantageous since by using it, 3T3 feeder cells which are necessary for stratifying corneal epithelial cells can be cultivated separately from the corneal epithelial cells. In this case, the corneal epithelial cells may be present on the cell insert or on the side of a dish where the cell insert is to be installed, provided that at least the surface where corneal epithelial cells are to be cultivated is covered with the temperature responsive polymer.

In the present invention, cell cultivation is effected on the cell culture support that has been prepared in the manner described above. The temperature of the culture medium is not limited in any particular way, except that it depends on whether the aforementioned polymer the substrate's surface has been covered with has an upper critical dissolution temperature or a lower critical dissolution temperature; in the former case, the medium's temperature should not be higher than the upper critical dissolution temperature and, in the latter case, it should not be less than the lower critical dissolution temperature. It goes without saying that it is inappropriate to perform cultivation in a lower-temperature range where the cultured cells will not grow or in a higher-temperature range where the cultured cells will die. The culture conditions other than temperature may be as adopted in the usual method and are not limited in any particular way. For instance, the culture medium to be used may be one that is supplemented with serum such as known fetal calf serum (FCS); alternatively, it may be a serum-free medium.

In the process of the present invention, the cultured cells may be detached and recovered from the support material by first bringing the cultured corneal epithelium forming cells into close contact with the carrier, then adjusting the temperature of the support material with adhering cells to either above the upper critical dissolution temperature of the overlying polymer on the support substrate or below its lower critical dissolution temperature, whereupon the cells can be detached together with the carrier. Detachment of the cell sheet can be effected within the culture solution in which the cells have been cultivated or in other isotonic fluids, whichever is suitable depending on the object.

In the present invention, the cell sheet as pressed against the diseased site may be stripped of the carrier. The method of stripping the carrier is not limited in any particular way and may be exemplified by a method in which the carrier is wetted so that its adhesion to the cell sheet is made sufficiently weak to enable stripping of the carrier or by a method in which the carrier is cut off by a suitable means such as a scalpel, scissors, laser light or plasma waves. Take, for example, the case of using the cell sheet placed in close contact with the aforementioned carrier having a cutout in a selected area; if the cell sheet is cut along the boundary of the diseased site as by laser light, the cell sheet will not adhere to any unwanted area that is outside of the diseased site, which is advantageous for the purposes of the invention.

The method of fixing the corneal epithelium forming cell sheet of the present invention to a living tissue is not limited in any particular way; the cell sheet may be sutured to the living tissue; alternatively, since the corneal epithelium forming cell sheet of the present invention will rapidly take on the living tissue, the cell sheet, once adhered to the diseased site, need not be sutured to the living body. In the latter case, it is particularly advisable to use a contact lens for the specific purpose of protecting the transplanted cell sheet.

The method of producing a stratified sheet which is another embodiment of the present invention is not limited in any particular way but may be exemplified by a method in which generally known 3T3 cells are grown as a feeder layer to effect stratification, or a method in which the corneal epithelium forming cell sheet in close contact with the aforementioned carrier is utilized to produce a stratified sheet. The following specific methods may be mentioned as examples.

(1) The cell sheet in close contact with the carrier is adhered to the cell culture support and, thereafter, the culture medium is added, whereby the carrier is stripped from the cell sheet, to which another cell sheet in close contact with the carrier is adhered, the process being repeated to form a stratified cell sheet.

(2) The cell sheet in close contact with the carrier is inverted and fixed on the cell culture support, with the carrier side facing down, and another cell sheet is adhered to the first cell sheet and, thereafter, the culture medium is added, whereby the carrier is stripped from the cell sheet, to which yet another cell sheet is adhered, the process being repeated to form a stratified cell sheet.

(3) Two cell sheets, each in close contact with the carrier, are held together in such a way that they face each other in close contact.

(4) A cell sheet in close contact with the carrier is pressed against the diseased site of a living body so that it is adhered to the living tissue and, thereafter, the carrier is stripped away and another cell sheet is superposed on the first cell sheet.

The stratified sheet of the present invention need not necessarily be made of corneal epithelium forming cells. It is also possible to superpose a corneal endothelial cell sheet and/or a conjunctival epithelial cell sheet that have been prepared by following the same procedure as in the case of the corneal epithelial cell sheet which is one version of the corneal epithelium forming cell sheet. This procedure is extremely effective for the purpose of creating a structure closer to anterior segment tissues in the living body.

In order to detach and recover the corneal epithelium forming cell sheet with high yield, the cell culture support may be lightly tapped or rocked or the culture medium may be agitated with the aid of a pipette; these and other methods may be applied either independently or in combination. In addition, the cultured cells may optionally be washed with an isotonic fluid or the like so that they are detached for recovery.

The use of the corneal epithelium forming cell sheet described in the present invention is not limited in any particular way and as already mentioned above, it may be used to treat not only diseased sites where the anterior segment tissue is partly or entirely damaged or deficient as in corneal erosion and corneal ulceration but also binocular refractory conjunctival diseases without corneal epithelial cells. Alternatively, the corneal epithelium forming cell sheet described in the present invention is effective in refraction corrective procedures such as: the PRK method in which excimer laser is applied to the center of the eye to ablate the surface of the cornea such that its refractive power is decreased to correct myopia; the LASIK method in which the corneal stromal layer is cut through a thickness of 160 μm with a microkeratome to make a flap, which is then turned over to ablate the corneal stromal layer with excimer laser and after smoothening its surface, the flap is returned to the initial position; and the LASEK method in which alcohol is dripped to soften the surface of the cornea and without using a microkeratome, the corneal epithelium is excised by a thickness of 50 μm to make a flap, which is then turned over to ablate the corneal stroma layer with excimer laser and after smoothening its surface, the flap is returned to the initial position.

The corneal epithelium forming cell sheet obtained by the process described above far excels what is obtained by the prior art methods in that it is non-invasive during detachment and has a great potential in clinical applications, as exemplified by corneal grafts. In particular, unlike the conventional graft sheets, the corneal epithelium forming cell sheet of the present invention has high take on living tissues and hence takes very rapidly on the living tissues. This contributes not only to improving the efficiency of treatment of a diseased site but also to reducing the burden on the patient, hence, it is anticipated to materialize as a very effective technique. Note that the cell culture support used in the process of the present invention allows for repeated use.

EXAMPLES

On the following pages, the present invention is described in greater detail by reference to examples which are by no means intended to limit the scope of the invention.

Example 1

To a commercial 6-well cell insert (FALCON 3090 manufactured by Beckton Dickinson Labware), a coating solution having N-isopropylacrylamide monomer dissolved in isopropyl alcohol to give a concentration of 30% was applied in a volume of 0.08 ml. By applying electron beams with an intensity of 0.25 MGy, an N-isopropylacrylamide polymer (PIPAAm) was immobilized on the surface of a culture dish. After the irradiation, the culture dish was washed with ion-exchanged water to remove the residual monomer and the PIPAAm that did not bind to the culture dish; the culture dish was then dried in a clean bench and sterilized with an ethylene oxide gas to provide a cell culture support material. The amount of the temperature responsive polymer on the substrate's surface was measured; as it turned out, the substrate was covered with 1.3 μg/cm$^2$ of the polymer.

On the obtained cell culture support material, normal rabbit corneal epithelial cells were cultivated by the usual method (medium used: CORNEPAK (product of KURABO INDUSTRIES, LTD.); 37° C. under 5% $CO_2$). As the result, the corneal epithelial cells adhered and grew normally on the cell culture support material.

At day 7 of the culture, the cells became confluent and were then cultivated for an additional 7 days; a carrier molded from a 2.1 cm$^\Phi$ polyvinylidene difluoride (PVDF) membrane having a 1.5 cm$^\Phi$ circular cutout in the center was placed over the cells; the culture medium was gently aspirated through the cutout and subjected to a low-temperature treatment by incubating and cooling at 20° C. for 30 minutes together with the cell culture support material, whereupon the cells on the cell culture support material were detached together with the overlying carrier. The cell sheet obtained had adequate strength as a single sheet, with a shrinkage of no more than 5%.

The corneal epithelial cell sheet obtained in Example 1 was transplanted in a rabbit (a pathologic model with corneal erosion) that was deficient of a corneal epithelial tissue portion by the usual method. The corneal epithelial cell sheet was adhered to the wounded site for 15 minutes and, thereafter, that portion of the cell sheet which overlapped the areas other than the diseased site was excised with a scalpel. After the excision, the cell sheet was not sutured to the living tissue. Three weeks later, the diseased site was observed and the corneal epithelial cell sheet was found to have taken well on the eyeball.

Example 2

In this Example, an N-isopropylacrylamide polymer (PIPAAm) was immobilized on the surface of a culture dish by repeating the procedure of Example 1, except that N-isopropylacrylamide monomer was dissolved in isopropyl alcohol to give a concentration of 35%. The amount of the temperature responsive polymer on the substrate's surface formed by the above method was measured; as it turned out, the substrate was covered with 1.5 μg/cm$^2$ of the polymer.

In this Example, corneal epithelial cells adhered and grew on the cell culture support material as normally as in Example 1. At day 7 of the culture, the cells became confluent and were then cultivated for an additional 7 days;

a carrier molded from a 2.1 cm$^\Phi$ polyvinylidene difluoride (PVDF) membrane having a 1.5 cm$^\Phi$ circular cutout in the center was placed over the cells; the culture medium was gently aspirated through the cutout and subjected to a low-temperature treatment by incubating and cooling at 20° C. for 30 minutes together with the cell culture support material, whereupon the cells on the cell culture support material were detached together with the overlying carrier. The cell sheet obtained had adequate strength as a single sheet, with a shrinkage of no more than 5%.

The corneal epithelial cell sheet obtained in Example 2 was transplanted in a rabbit (a pathologic model with corneal erosion) that was deficient of a corneal epithelial tissue portion by the usual method. The corneal epithelial cell sheet was adhered to the wounded site for 15 minutes and, thereafter, that portion of the cell sheet which overlapped the areas other than the diseased site was excised with a scalpel. After the excision, the cell sheet was not sutured to the living tissue but a contact lens was mounted on the diseased site after the cell sheet was grafted. Three weeks later, the diseased site was observed and the corneal epithelial cell sheet was found to have taken well on the eyeball.

Example 3

By repeating the procedure of Example 1, normal rabbit corneal epithelial cells were cultivated on the same cell culture support, except that the medium was changed to the ordinary medium of Green et al. containing mitomycin C (DMEM+AB (for making a feeder layer); for human neonatal keratinized epithelial cells). As the result, the corneal epithelial cells adhered and grew normally on the cell culture support material.

At day 6 of the culture, the cells became confluent and were then cultivated for an additional 6 days until they stratified. Subsequently, a carrier molded from a 2.1 cm$^\Phi$ polyvinylidene difluoride (PVDF) membrane having a 1.5 cm$^\Phi$ circular cutout in the center was placed over the cells; the culture medium was gently aspirated through the cutout and subjected to a low-temperature treatment by incubating and cooling at 20° C. for 30 minutes together with the cell culture support material, whereupon the stratified, corneal epithelial cell sheet on the cell culture support material was detached together with the overlying carrier. The detached stratified sheet had adequate strength as a single sheet, with a shrinkage of no more than 5%.

The stratified, corneal epithelial cell sheet obtained in Example 3 was transplanted in a rabbit (a pathologic model with corneal erosion) that was deficient of a corneal epithelial tissue portion by the usual method. The corneal epithelial cell sheet was adhered to the wounded site for 15 minutes and, thereafter, that portion of the cell sheet which overlapped the areas other than the diseased site was excised with laser light. After the excision, the cell sheet was not sutured to the living tissue. Three weeks later, the diseased site was observed and the stratified, corneal epithelial cell sheet was found to have taken well on the eyeball.

Comparative Example 1

A corneal epithelial cell sheet was prepared as in Example 1, except that the cell sheet was detached without using the carrier, whereupon it shrank by 42%.

As in Example 1, the corneal epithelial cell sheet obtained was transplanted in a rabbit that was deficient of a corneal epithelial tissue portion by the usual method. The corneal epithelial cell sheet was adhered to the wounded site for 15 minutes and, thereafter, that portion of the cell sheet which overlapped the areas other than the diseased site was excised with a scalpel. After the excision, the cell sheet was not sutured to the living tissue. At day 1 of the grafting, the diseased site was observed; the corneal epithelial cell sheet took only poorly on the eyeball and would come off the diseased site at any moment.

Comparative Example 2

A stratified, corneal epithelial cell sheet was prepared as in Example 3, except that the cell sheet was detached from the cell culture support 28 days after confluence was reached. The sheet obtained shrank by no more than 5% and had adequate strength as a single sheet.

Then, as in Example 3, the stratified, corneal epithelial cell sheet obtained was transplanted in a rabbit that was deficient of a corneal epithelial tissue portion by the usual method. The corneal epithelial cell sheet was adhered to the wounded site for 15 minutes and, thereafter, that portion of the cell sheet which overlapped the areas other than the diseased site was excised with a scalpel. After the excision, the cell sheet was not sutured to the living tissue. At day 1 of the grafting, the diseased site was observed; the corneal epithelial cell sheet took only poorly on the eyeball and would come off the diseased site at any moment.

Example 4

To a commercial 3.5 cm$^\Phi$ cell culture dish (FALCON 3001 manufactured by Beckton Dickinson Labware), a coating solution having N-isopropylacrylamide monomer dissolved in isopropyl alcohol to give a concentration of 30% was applied in a volume of 0.1 ml. By applying electron beams with an intensity of 0.25 MGy, an N-isopropylacrylamide polymer (PIPAAm) was immobilized on the surface of the culture dish. After the irradiation, the culture dish was washed with ion-exchanged water to remove the residual monomer and the PIPAAm that did not bind to the culture dish; the culture dish was then dried in a clean bench and sterilized with an ethylene oxide gas to provide a cell culture support material. The amount of the temperature responsive polymer on the substrate's surface was measured; as it turned out, the substrate was covered with 1.4 µg/cm$^2$ of the polymer.

In a separate step, a white rabbit as a model of keratoconjunctival epitheliopathy had been prepared by the usual method. An oral mucosal tissue was collected from the rabbit under deep anesthesia and its epithelial cells were cultivated on the obtained cell culture support material by the usual method together with 3T3 cells (medium used: CORNEPAK (product of KURABO INDUSTRIES, LTD.); 37° C. under 5% $CO_2$). As the result, all epithelial cells adhered and grew normally on the cell culture support material.

At day 6 of the culture, the cells became confluent and were then cultivated for an additional 7 days; a carrier molded from a 2.3 cm$^\Phi$ polyvinylidene difluoride (PVDF) membrane having a 1.8 cm$^\Phi$ circular cutout in the center was placed over the cells; the culture medium was gently aspirated through the cutout and subjected to a low-temperature treatment by incubating and cooling at 20° C. for 30 minutes together with the cell culture support material, whereupon the cells on the cell culture support material were detached together with the overlying carrier. The cell sheet obtained had adequate strength as a single sheet, with a shrinkage of no more than 5%.

The oral mucosal cell sheet obtained in Example 4 was transplanted in a white rabbit (a model of keratoconjunctival epitheliopathy) that was deficient of a corneal epithelial tissue portion by the usual method. The oral mucosal cell sheet was adhered to the wounded site for 15 minutes and, thereafter, that portion of the cell sheet which overlapped the areas other than the diseased site was excised with a scalpel. After the excision, the cell sheet was not sutured to the living tissue. Three weeks later, the diseased site was observed and the oral mucosal cell sheet was found to have taken well on the eyeball.

Example 5

In this Example, an N-isopropylacrylamide polymer (PIPAAm) was immobilized on the surface of the culture dish by repeating the procedure of Example 4, except that N-isopropylacrylamide monomer was dissolved in isopropyl alcohol to give a concentration of 35%. The amount of the temperature responsive polymer on the substrate's surface formed by the above method was measured; as it turned out, the substrate was covered with 1.5 $\mu g/cm^2$ of the polymer.

In this Example, oral mucosal epithelial cells adhered and grew on the cell culture support material as normally as in Example 4. At day 6 of the culture, the cells became confluent and were then cultivated for an additional 7 days; a carrier molded from a 2.3 $cm^\Phi$ polyvinylidene difluoride (PVDF) membrane having a 1.8 $cm^\Phi$ circular cutout in the center was placed over the cells; the culture medium was gently aspirated through the cutout and subjected to a low-temperature treatment by incubating and cooling at 20° C. for 30 minutes together with the cell culture support material, whereupon the cells on the cell culture support material were detached together with the overlying carrier. The cell sheet obtained had adequate strength as a single sheet, with a shrinkage of no more than 5%.

The oral mucosal cell sheet obtained in Example 5 was transplanted in a white rabbit (a model of keratoconjunctival epitheliopathy) that was deficient of a corneal epithelial tissue portion by the usual method. The oral mucosal cell sheet was adhered to the wounded site for 15 minutes and, thereafter, that portion of the cell sheet which overlapped the areas other than the diseased site was excised with a scalpel. After the excision, the cell sheet was not sutured to the living tissue but a contact lens was mounted on the diseased site after the cell sheet was grafted. Three weeks later, the diseased site was observed and the oral mucosal cell sheet was found to have taken well on the eyeball.

Example 6

The procedure of Example 4 was repeated to perform cell cultivation on the same cell culture support material, except that epithelial stem cells were collected from the hair root tissue of the skin of a white rabbit under deep anesthesia and were cultivated together with 3T3 cells. As the result, the hair root cells adhered and grew normally on the cell culture support material. After 2-week cultivation, a carrier molded from a 2.1 $cm^\Phi$ polyvinylidene difluoride (PVDF) membrane having a 1.5 $cm^\Phi$ circular cutout in the center was placed over the cells; the culture medium was gently aspirated through the cutout and subjected to a low-temperature treatment by incubating and cooling at 20° C. for 30 minutes together with the cell culture support material, whereupon the stratified, corneal epithelial cell sheet on the cell culture support material was detached together with the overlying carrier. The detached stratified sheet had adequate strength as a single sheet, with a shrinkage of no more than 5%.

The cell sheet obtained in Example 6 was transplanted in a white rabbit (a model of keratoconjunctival epitheliopathy) that was deficient of a corneal epithelial tissue portion by the usual method. The hair root cell sheet was adhered to the wounded site for 15 minutes and, thereafter, that portion of the cell sheet which overlapped the areas other than the diseased site was excised with laser light. After the excision, the cell sheet was not sutured to the living tissue. Three weeks later, the diseased site was observed and the cell sheet was found to have taken well on the eyeball.

Example 7

The procedure of Example 4 was repeated to perform cell cultivation on the same cell culture support material, except that conjunctival epithelial cells were collected from the conjunctival tissue of the skin of a white rabbit under deep anesthesia and were cultivated together with 3T3 cells. As the result, the conjunctival epithelial cells adhered and grew normally on the cell culture support material. After 2-week cultivation, a carrier molded from a 2.1 $cm^\Phi$ polyvinylidene difluoride (PVDF) membrane having a 1.5 $cm^\Phi$ circular cutout in the center was placed over the cells; the culture medium was gently aspirated through the cutout and subjected to a low-temperature treatment by incubating and cooling at 20° C. for 30 minutes together with the cell culture support material, whereupon the stratified, corneal epithelial cell sheet on the cell culture support material was detached together with the overlying carrier. The detached stratified sheet had adequate strength as a single sheet, with a shrinkage of no more than 3%.

The cell sheet obtained in Example 7 was transplanted in a white rabbit (a model of keratoconjunctival epitheliopathy) that was deficient of a corneal epithelial tissue portion by the usual method. The hair root cell sheet was adhered to the wounded site for 15 minutes and, thereafter, that portion of the cell sheet which overlapped the areas other than the diseased site was excised with laser light. After the excision, the cell sheet was not sutured to the living tissue. Three weeks later, the diseased site was observed and the stratified conjunctival cell sheet was found to have taken well on the eyeball, with no visible neovascularization from the conjunctiva.

Comparative Example 3

An oral mucosal cell sheet was prepared as in Example 4, except that the cell sheet was detached without using the carrier, whereupon it shrank by 38%.

As in Example 4, the oral mucosal cell sheet obtained was transplanted in a rabbit that was deficient of a corneal epithelial tissue portion by the usual method. The oral mucosal cell sheet was adhered to the wounded site for 15 minutes and, thereafter, that portion of the cell sheet which overlapped the areas other than the diseased site was excised with a scalpel. After the excision, the cell sheet was not sutured to the living tissue. At day 1 of the grafting, the diseased site was observed; the oral mucosal cell sheet took only poorly on the eyeball and would come off the diseased site at any moment.

From the foregoing results, it became clear that using the procedure of the present invention, one can fabricate corneal epithelium substitute cell sheets having good adherence to the anterior segment tissue. This contributes to reducing the burden on patients by making the treatment protocol simpler and more efficient; in addition, since those cell sheets assure a full coverage and positive adherence to the diseased site, the present invention is believed to provide a very effective technique that enables marked reduction of the pain felt by the patients.

Example 8

A stratified, corneal epithelial cell sheet in close contact with a carrier was prepared by a method identical to the procedure shown in Example 3. A test was made to see whether the sheet would be a substitute for the corneal epithelial flap in the LASIK method known as a corrective procedure for the treatment of myopia.

Specifically, the cornea of a rabbit was subjected to the test; the corneal stromal layer was cut through a thickness of 160 μm with a microkeratome to make a flap, which was then removed to ablate the corneal stromal layer with excimer laser and after smoothening its surface, the stratified, corneal epithelial cell sheet in close contact with the carrier that had been prepared in accordance with Example 3 was adhered to the position which the flap should be returned to. To end the grafting procedure, the stratified, corneal epithelial cell sheet was cut to the same size as the diseased site by means of laser light. No suturing was done. Three weeks later, the diseased site was observed and the stratified, corneal epithelial cell sheet was found to have taken well on the eyeball; it was therefore concluded that the stratified, corneal epithelial cell sheet of the present invention was also effective in the LASIK method.

Example 9

A stratified, corneal epithelial cell sheet in close contact with a carrier was prepared by a method identical to the procedure shown in Example 3. A test was made to see whether the sheet would be a substitute for the corneal epithelial flap in the LASEK method also known as a corrective procedure for the treatment of myopia.

Specifically, the cornea of a rabbit was subjected to the test; alcohol was dripped to soften the surface of the cornea and without using a microkeratome, the corneal epithelium was excised by a thickness of 50 μm to make a flap, which was then removed to ablate the corneal stromal layer with excimer laser and after smoothening its surface, the stratified, corneal epithelial cell sheet in close contact with the carrier that had been prepared in accordance with Example 3 was adhered to the position which the flap should be returned to. To end the grafting procedure, the stratified, corneal epithelial cell sheet was cut to the same size as the diseased site by means of laser light. No suturing was done. Three weeks later, the diseased site was observed and the stratified, corneal epithelial cell sheet was found to have taken well on the eyeball; it was therefore concluded that the stratified, corneal epithelial cell sheet of the present invention was also effective in the LASEK method.

From the foregoing results, it became clear that using the procedure of the present invention, one can fabricate regenerated corneal epithelial cell sheets, both single-layered and stratified, having good adherence to the anterior segment tissue. This is believed to provide a very effective technique which contributes to reducing the burden on patients by making the treatment protocol simpler and more efficient.

INDUSTRIAL APPLICABILITY

The corneal epithelium forming cell sheets obtained by the present invention feature very high take, or "high adherence", to living tissues and have a great potential for use in clinical applications including corneal grafting, treatment of corneal diseases, and treatment of myopia. Hence, the present invention will prove very useful in medical and biological fields such as cell engineering and medical engineering.

The invention claimed is:

1. A method of treating a patient at a diseased site where an anterior segment tissue is partly or entirely damaged or deficient, the method comprising steps of:
   cultivating corneal epithelium forming cells on a cell culture support comprising a substrate having its surface covered with a temperature responsive polymer having a hydrating force that varies in a temperature range of 0° C.-80° C. with respect to water to form a cell sheet, wherein the corneal epithelium forming cells comprise oral mucosa cells that originate from buccal membrane;
   and thereafter,
   (1) adjusting the temperature of the culture solution to either above an upper critical dissolution temperature or below a lower critical dissolution temperature,
   (2) bringing the cell sheet into close contact with a carrier, wherein the carrier is of annular shape having a cutout in the center,
   (3) detaching the cell sheet together with the carrier from the cell culture support,
   (4) grafting the cell sheet to the diseased site, and
   (5) removing the carrier from the cell sheet grafted on the diseased site.

2. The method of treatment according to claim 1, wherein the grafted sheet covers the diseased site without suturing.

3. The method of treatment according to claim 1, wherein the disease to be treated is corneal erosion, corneal ulceration, or a binocular refractory conjunctival disease.

4. The method of treatment according to claim 1, wherein the treatment involves refractive correction by radial keratotomy (RK), photorefractive keratectomy (PRK), laser assisted in situ keratomileusis (LASIK), or laser assisted subepithelial keratectomy (LASEK).

5. The method according to claim 1, wherein the detachment of the cell sheet is conducted without proteinase treatment.

6. The method according to claim 1, wherein the corneal epithelium forming cells are cultivated in the presence of feeder cells, thereby stratifying the cell sheet.

7. The method according to claim 1, wherein the detached cell sheet obtained in the step of (3) is adhered to another cell sheet, thereby stratifying the cell sheet.

* * * * *